United States Patent [19]

Sommermeyer

[11] Patent Number: 5,492,713
[45] Date of Patent: Feb. 20, 1996

[54] NUTRIMENT PREPARATION

[76] Inventor: Klaus Sommermeyer, Kapersburgstrasse 6b, 61191, Rosbach f.d.H., Germany

[21] Appl. No.: 150,039
[22] PCT Filed: May 13, 1992
[86] PCT No.: PCT/EP92/01049
§ 371 Date: Aug. 5, 1994
§ 102(e) Date: Aug. 5, 1994
[87] PCT Pub. No.: WO92/20241
PCT Pub. Date: Nov. 26, 1992

[30] Foreign Application Priority Data

May 16, 1991 [DE] Germany .......................... 41 16 004.5

[51] Int. Cl.⁶ .................................................. A23D 9/007
[52] U.S. Cl. ............................................ 426/601; 426/606
[58] Field of Search .................................... 426/601, 606

[56] References Cited

U.S. PATENT DOCUMENTS 3,579,548  5/1971  Whyte .

FOREIGN PATENT DOCUMENTS

| 0216419 | 4/1987 | European Pat. Off. . |
| 0367734 | 9/1989 | European Pat. Off. . |
| 0404214 | 5/1990 | European Pat. Off. . |
| 0366480 | 5/1990 | European Pat. Off. . |
| 0391431 | 10/1990 | European Pat. Off. . |
| 1600887 | 9/1970 | France . |
| 9012080 | 10/1990 | WIPO . |
| 9103944 | 4/1991 | WIPO . |
| 9220241 | 11/1992 | WIPO . |

OTHER PUBLICATIONS

Patton 1976 Biomedical Aspects of Lactation Pergamon Press New York pp. 88–91.

*Primary Examiner*—Carolyn Paden
*Attorney, Agent, or Firm*—Whitham, Curtis, Whitham & McGinn

[57] ABSTRACT

The present invention concerns nutriment preparations for humans and animals which are suited in particular for ureamic patients and for clinical nutrition and which contain as an energy substrate at least one glycerid hard to dissolve resp. insoluble in water with at least one branched-chain fatty acid derived from the residue of the general Formula II

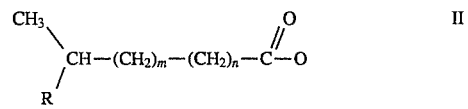

wherein R designates a methyl residue or an ethyl residue, m designates 0 or 1, preferably 1, and n designates 0 or an even number between 2 and 18, preferably 0 or an even number between 2 and 6 and in particular 0, 2 or 4. The preparations according to the invention are suited for the treatment of severe trauma and sepsis and, in particular, for the treatment of ureamic patients, e.g. during chronic kidney insufficiency, of urea synthesis disorders and for nutrition therapy of acute kidney failure. The preparations may be administered both enterally and parenterally, whereby the customary administration forms, e.g. emulsions or oil capsules, are suitable. In addition, they may be used as supplements of the normal diet or in any other coventional preparation form.

16 Claims, No Drawings

NUTRIMENT PREPARATION

BACKGROUND OF THE INVENTION

The present invention concerns a nutriment preparation for humans and animals comprising an energy substrate which is suited in particular for uraemic patients and for clinical nutrition.

Patients who must be nourished clinically often display a poor standard of nutrition such as that obtaining in the case of severe trauma, for example severe and extensive burns, operative trauma, severe physical injuries, different forms of cancer or sepsis. In such conditions, the metabolism picture is complicated.

In the metabolism of the body a number of metabolites which are subject to further oxidation and thereby produce different amounts of energy are synthesized from carbohydrates and fats. The ketone bodies which represent important alternative energy substrates for the body are examples of such metabolites. In the condition of hunger they are created in large quantities, and in the case of a prolonged hunger condition they become more important than glucose as an energy source. The possibility of utilizing ketone bodies to prevent the damaging decomposition (catabolism) of muscular protein for gluconeogenesis thereby reduces the loss of valuable body protein and thus exerts an energy-saving effect.

In the peripheral protein depots (muscles) mainly the branched-chain amino acids leucine, isoleucine and valine, in the main leucine, are oxidized, which means that in these patients the pool of branched-chain amino acids is gradually exhausted, which in turn results in reduced protein synthesis in the liver.

Ketone bodies have thus become increasingly interesting as an energy substrate both in enteral and parenteral nutrition, beyond their current administration in dialysis patients resp. patients displaying restricted kidney function.

Numerous experiments have already been conducted to find a method by which ketone bodies and similar substances may be effectively administered to the body. The branched-chain keto-acids, in particular ketoleucine, ketoisoleucine and ketovaline, are of special interest in this regard.

However, for a number of reasons the possibility of administering keto-acids is limited. They are practically not processable in aqueous solution, since they display very minimal stability and, moreover, they also cause very considerable strain. In addition, they must be administered in the form of salts, which entails the risk that excessive quantities of cations, for example sodium cations and potassium cations, are ingested during their administration. Furthermore, keto-acids and their salts are soluble in water and thereby raise the osmotic pressure of the nutriment, which causes the corresponding deleterious effects, such as too rapid passage through the bowels and diarrhea.

A circumvention of these problems is achieved by the somewhat more stable branched-chain α-hydroxy acids, which, however, were initially only administered as unazotized amino acid substitutes. According to the PCT-Application WO 90/02547, α-hydroxy acids and their pharmaceutically acceptable metal salts are used as precursors of the branched-chain keto-acids. These α-hydroxy acids are used metabolically as an energy substrate in enteral and parenteral nutrition after respective metabolization.

In the EP 0 367 734 energy substrates for clinical nutrition were used, which contain at least one ester of glycerine and at least one branched-chain hydroxycarbon acid. L-α-hydroxyisocapronic acid, α-hydroxy-β-methylvaleric acid and L-α-hydroxyisovaleric acid were named as examples of such hydroxycarbon acids.

The use of triglycerides with less calories in nutriments is proposed in the PCT-Application WO 91/03944, whereby the calory ingestion is to be reduced simultaneously with nutriment ingestion. In the triglycerides designed for this purpose, the hydroxy groups in position 1 and 3 of the glycerol are estered with saturated long-chain fatty acids (16–40 carbon atoms) and the hydroxy group in position 2 of the glycerol is estered with a short-chain acid (2–10 carbon atoms), which may be either saturated or unsaturated or straight- or branched-chain.

The use of glycerol esters in nutriment mixtures for the treatment of obesity is also known from the U.S. Pat. No. 3,579,548. The glycerol esters used there are glycerol esters of α-branched-chain carbon acid. With these triglycerides few calories are to be provided, i.e. these triglycerides are not to be digested and absorbed to the same extent as conventional triglycerides.

According to the FR-Patent 1.600,887 glycerine-triisobutyrate is proposed as a component of nutriments, in particular of nutriments for brood animals.

SUMMARY OF THE INVENTION

According to the invention it was surprisingly found that glycerides hard to dissolve in water or practically insoluble in water of the general Formula I

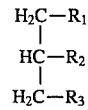

whereby one of the residues $R_1$, $R_2$ or $R_3$ may designate a hydroxy residue or a residue of a saturated or unsaturated fatty acid with 2 to 24 carbon atoms and two or three of the residues $R_1$, $R_2$ or $R_3$ designate a residue of the general Formula II

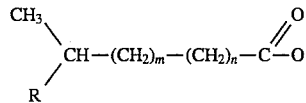

whereby R designates a methyl residue or an ethyl residue, m designates 0 or 1 and n designates 0 or an even number from 2 to 18, represent excellent energy substrates for humans and animals, in particular for uraemic patients, and are suitable for clinical nutrition and do not display the disadvantages specified above.

These glycerides are stable compounds which are easy to handle. They are hard to dissolve in water resp. practically water-insoluble and thus do not exert osmotic pressure. They are only transformed in the body in the course of their metabolization, e.g. through α- and/or β-oxidation, into the corresponding hydroxy-analogous fatty acids, in particular the hydroxy-analogues of the branched-chain amino acids, from which the corresponding branched-chain keto-acids, which are used metabolically as an energy substrate, are formed after corresponding metabolization. They may also be transaminated into the corresponding branched-chain L-amino acids enzymatically under decomposition of the urea pool which is enlarged in ureamic patients. They facilitate the reutilization of decomposition products containing nitrogen, protein anabolism with simultaneous reduction of the serum urea as well as an improvement of the nitrogen balance and thus an improvement of the ureamic symptoms, whereby dialysis can possibly be deferred.

A protein-saving effect was thus achieved by means of the preparations according to the invention.

Further advantages of the glycerides used according to the invention are to be seen in the kinetics of the metabolization, since the ketone bodies cannot rise as excessively as in therapy with hydroxy-analogous compounds. In addition, the metabolization of the medium-chain glycerides is not carnitine-dependent.

The production of the glycerides used according to the invention occurs in known manner, as described for example in "Analyse der Fette und Fettprodukte einschließlich der Wachse, Harze und verwandten Stoffe", H. P. Kaufmann, Springer Verlag, 1958. The glycerides used according to the invention are also easy to process by the known technologies for producing fat emulsions and, as a major advantage, present no stability problems of any kind.

DETAILED DESCRIPTION OF THE INVENTION

The glycerides used in the preparations according to the invention possess the general Formula I $$
\begin{array}{l}
H_2C-R_1 \\
HC-R_2 \\
H_2C-R_3
\end{array}
$$

wherein one of the residues $R_1$, $R_2$ or $R_3$ may designate a hydroxy residue or a residue of a saturated or unsaturated fatty acid with 2 to 24 carbon atoms and two or three of the residues $R_1$, $R_2$ or $R_3$ designate a residue of the general Formula II

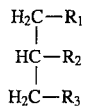

II whereby R designates a methyl residue or an ethyl residue, m designates 0 or 1 and n designates 0 or an even number from 2 to 18.

In the general Formula II, m preferably designates 1 and n designates 0 or an even number from 2–6, in particular 0, 2 or 4.

Examples of suitable residues of the Formula II are the residues of the Formulae III to V

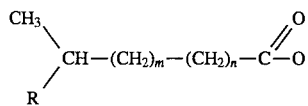

III

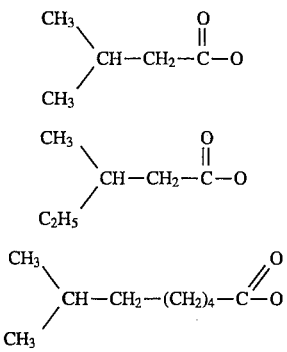

from which the corresponding α-hydroxy acids are formed in the body after respective metabolization, e.g. after respective α- and/or β-oxidation, and are then transformed into the corresponding α-keto analogues, i.e. ketovaline, ketoisoleucine resp. ketoleucine.

If the residues $R_1$, $R_2$ and/or $R_3$ are derived from the Formula I of anteiso fatty acids, then they are preferably derived from the L-form of these acids.

In the general Formula I all three residues $R_1$, $R_2$ and $R_3$ designate a residue of the general Formula II, whereby the residues $R_1$, $R_2$ and $R_3$ may designate the same residue of the general Formula II or different residues of the general Formula II. Preferably all residues $R_1$, $R_2$ or $R_3$ designate the same residue of the general Formula II.

Specific examples of glycerides used in the preparations according to the invention are

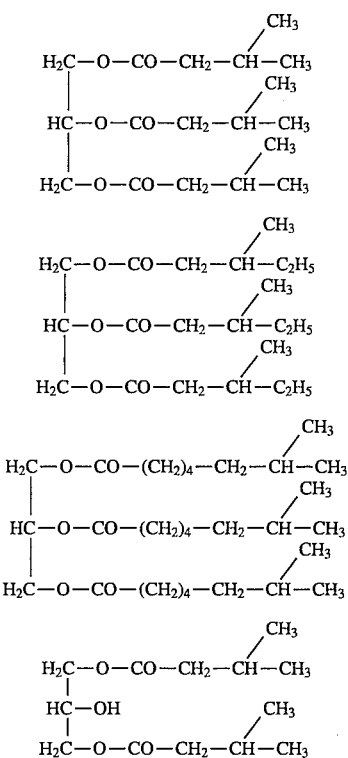

Mixtures of the glycerides among each other may also be used.

The glycerides contained in the preparations according to the invention may also be present resp. used in the form of animal fats and/or oils. For example, the may be present in the form of fish oil and/or ruminant fat or in the form of fractions of these fats and/or oils, in which the triglycerides containing the branched fatty acids are enriched.

The preparations according to the invention contain the glycerides in a quantity of 0.2 to 100% (weight/volume), preferably in a quantity of 0.2 to 35% (weight/volume).

The preparations according to the invention may be administered both enterally and parenterally. The administration methods usually employed, e.g. emulsions or oil capsules, may be used for administration.

The glycerides used according to the invention are oily substances. The may be used alone or together with known conventional pharmaceutically tolerable substances. Since they are hard to solve in water resp. insoluble in water, they must be transformed into an emulsion, in particular for intravenous infusion. The glycerides are only suitable for transformation into an emulsion to the extent that they possess sufficient insolubility in water. The production of the emulsion occurs in known manner according to known technologies, as described, for example, in the DE-Patent 37 22 540. The emulsions according to the invention are stable and display compositions and properties which permit both enteral and parenteral administration in humans and animals. To produce the emulsion, a sterile, pyrogen free water phase is suitably used. Suitable emulgators are phospholipides of vegetable or animal origin resp. fractions of these substances. Preferably, a fractioned egg lecithin is used. Glycerol or other pharmaceutically acceptable polyoles, such as e.g. sorbite, are used as auxiliary substances for isotonization of the outer aqueous phase.

Suitable coemulgators are sodium or potassium salts of longer-chained fatty acids, e.g. sodium or potassium salts of oleic acid, palmitic acid or stearic acid.

The emulsions may also contain amino acids, fats of synthetic, vegetable or animal origin, carbohydrates, vitamins and/or trace elements. Soy oil, saflore oil, olive oil, cottonseed oil and triglycerides with unbranched medium carbon chain (MCT) and/or other physiologically acceptable triglycerides of vegetable, animal or synthetic origin are examples of suitable fats. An addition of highly fractioned fish oils is thereby preferred, since they contain low quantities of suitable branched-chain triglycerides and are thus utilized as natural sources of branched-chain triglycerides. In addition, fat fractions of depot fats of ruminants may also be employed to the same effect. The use of triglyceride fractions from these two preferred animal sources also has the advantage that the L-form of the branched-chain anteiso fatty acids is thereby present, such as that for example also present in the assymetrical C-atom of the alkyl chain of isoleucine. These fats may be present in the emulsions in a quantity of 2 to 30%.

The preparations according to the invention my also contain 0.5 to 10% acetylized mono- or diglycerides of saturated or unsaturated fatty acids with 6 to 24 carbon atoms.

Emulsions represent the preferred form of the preparations according to the invention and may be administered parenterally or enterally. The glycerides resp. the preparations according to the invention may, however, also be used as supplements to the normal diet or in any other suitable preparation form. Oil capsules are a further suitable preparation form, whereby the capsules consist of gelatine, e.g. soft gelatine, or another suitable material.

The glycerides used in the preparations according to the invention are well tolerated and non-toxic in the doses usually applicable.

The preparations according to the invention are administered to humans and animals in catabolic condition. They are suitable for the treatment of severe trauma and sepsis and, in particular, for the treatment of ureamic patients, for example for kidney insufficiency, urea synthsis disorders and for nutrition therapy of acute kidney failure.

EXAMPLE 1

Production of Glyceryl Triisolvalerate

In a reaction vessel fitted with a stirring apparatus and a reflux cooler with a water separator, 1 mol glycerol and 5 ml concentrated sulfuric acid were mixed with 3.5 mol isovaleric acid under stirring and heated under reflux, whereby 700 ml benzene were added for water removal. The reaction product obtained was purified in conventional manner. It was examined by gas chromatography as to identity and purity and thereby conformed to the literature sources bp=330–5$^{763}$, d=0.9984$_4^{20}$, nD=1.435.

EXAMPLE 2

Production of Glyceryl Tri(3-methylvalerate)

The process according to Example 1 was repeated, except that 3-methylvaleric acid was used in place of isovaleric acid.

EXAMPLE 3

Production of Glyceryl Tri(4-methylvalerate)

The process according to Example 1 was repeated, except that 4-methylvaleric acid was used in place of isovaleric acid.

EXAMPLE 4

Production of Oil Capsules

The compound produced according to Example 1 was inserted in soft gelatine capsules, whereby 0.5 g of the compound ware used per capsule.

EXAMPLE 5

Production of an emulsion of the following composition:
100 g high-fraction fish oil
100 g glyceryl triisovalerate
12 g egg lecithin, fractioned
0.3 g sodium oleate
25 g glycerol (anhydrous)
ad 1000 ml aqua ad injectabilia An emulsion was produced using the above components, whereby it was ensured that the components and mixtures were continuously maintained in nitrogen atmosphere. 12 g egg lecithin were added to 75 ml distilled water of 55° to 60° C. temperature for injection purposes during app. 2 minutes under constant stirring. The mixture obtained was stirred for another 15 minutes. In parallel, 25 g glycerol (100%) and 0.3 g sodium oleate were added to 25 ml distilled water for injection purposes also heated to 55° to 60° C. and gradually dissolved by stirring. The solution obtained was further maintained at 55° to 60° C. and added to the prepared water-lecithin mixture in 10 minutes through an 0.2 μm membrane filter. 100 g triglyceride were heated to 55° to 60° C. and directly added to the prepared aqueous mixture of lecithin, glycerol and sodium oleate through a nylon membrane filter with a pore size of 0.2 μm within 20 to 25 minutes under constant stirring, e.g. by using a mechanical high-frequency appliance (Ultra-Turrax) for emulgation together with a stirring apparatus. After the addition of the glyceride was completed the raw emulsion thus formed Was emulgated for further 25 minutes. During production of the raw emulsion the latter was maintained at 60° to 65° C. and constantly overlaid with nitrogen.

After the mechanical high-frequency appliance was switched off, the raw emulsion was transferred under slight stirring to a two-stage homogenisator (first stage 400 bar, second stage 100 bar) suitable for the production of fat emulsions, through a membrane filter with an average pore size of 40 μm under a nitrogen pressure of app. 0.5 bar and homogenized. After the first homogenization step the temperature was app. 70° C. and after the second homogenization step it was app. 80° C. The emulsion was subsequently cooled to 70° C. and transferred into a storage tank overlaid with nitrogen. The emulsion was left to rest under occasional slow stirring. Then the emulsion was subjected to two further homogenization steps, whereby the temperature reached 75° C. after the third and 80° to 85° C. after the fourth homogenization step. Subsequently the emulsion was cooled as much as possible and tranferred into a receiver containing 757 ml distilled water cooled to 12° C. This process was also carried out in nitrogen atmosphere. The emulsion was further cooled to 8° to 9° C. under occasional slow stirring. After this temperature was reached, the stirring apparatus was switched off.

The pH-value or the emulsion was examined, deviations from the nominal value (pH-value or 8.7 to 8.8) were corrected by addition of a corresponding amount 1 n NaOH. The rat emulsion obtained was stored in a cooling tank under nitrogen atmosphere and filtered through a membrane filter with a pore size of 2 to 8 μm before filling. The filling pressure was 0.5 bar max. The filling was carried out into glass containers which were subsequently closed. The fat emulsions must be protected against light and oxygen. The filling was carried out under nitrogen, so as to ensure that the oxygen content in the containers was kept as low as possible.

EXAMPLE 6

A nutriment preparation wherein the glyceride content was 5 to 15% was prepared using glyceryl triisovalerate. The composition of the nutriment preparation was as follows:

| | | |
|---|---|---|
| Milk and soy protein | 3.8 | g |
| Glyceryl triisovalerate | 5 | g |
| Essential fatty acids | 1.6 | g |
| Glucose | 0.1 | g |
| Maltose | 0.4 | g |
| Raw sugar | 3.0 | g |
| Polysaccharide | 10.2 | g |
| Na | 3.3 | mmol |
| K | 3.2 | mmol |
| Cl | <3.3 | mmol |
| Ca | 50 | mg |
| Mg | 13 | mg |
| P | 60 | mg |
| Fe | 1.0 | mg |
| Zn | 0.75 | mg |
| Cu | 0.15 | mg |
| Jodine | 7.5 | μg |
| Water added to 100 ml. | | |

This nutriment preparation may still be supplemented by the daily requirement of water-soluble and fat-soluble vitamins.

I claim:

1. Nutriment preparation, comprising:

a glyceride having the general formula:

$$\begin{array}{c} CH_2-R_1 \\ | \\ CH-R_2 \\ | \\ CH_2-R_3 \end{array}$$

wherein $R_{1-3}$ may be the same or different and are selected from the group consisting of hydroxy residues, saturated or unsaturated fatty acid residues having 2 to 24 carbon atoms, and metabolite residues whereby at least two of said residues $R_{1-3}$ are metabolite residues, and wherein said metabolite residues may be the same or different and have the chemical formula:

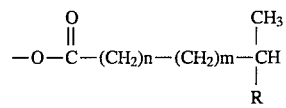

where R is selected from the group consisting of methyl and ethyl residues, m is 0 or 1, and n is 0 or an even number from 2 to 18 provided that when m equals 0 n is greater than or equal to 2 and when n equals 0 m equals 1.

2. Preparation according to claim 1, characterized in that m designates 1 and n designates 0 or an even number from 2 to 6.

3. Preparation according to claim 2, characterized in that n designates 0, 2 or 4.

4. Preparation according to claim 1, wherein all residues $R_1$, $R_2$, and $R_3$ each designate a residue of the Formula:

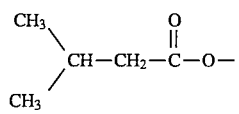

5. Preparation according to claim 1 wherein all residues $R_1$, $R_2$, and $R_3$ each designate a residue of the Formula

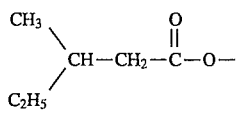

6. Preparation according to claim 1, wherein said glyceride is present in a quantity of 0.2–100% (weight/volume).

7. Preparation according to claim 6, characterized in that it contains the glyceride in a quantity of 0.2–35% (weight/volume).

8. Preparation according to claim 1, comprising a mixture of at least two different glycerides of said glycerides.

9. Preparation according to claim 1, wherein said glycerides are present in a form selected from the group consisting of a combination of animal fats and oils, animal fats, oils, and fractions thereof which are enriched by triglycerides containing branched fatty acids.

10. Preparation according to claim 9, wherein said glycerides are present in the form selected from the group consisting of a combination of fish oil and ruminant fat, fish oil, and ruminant fat.

11. Preparation according to claim 10, characterized in that said glycerides are present in the form of said fractions of said fats and oils enriched by said triglycerides containing branched fatty acids.

12. Preparation according to claim 9, characterized in that said glycerides are present in the form of said fractions of said fats and oils enriched by said triglycerides containing branched fatty acids.

13. Preparation according to claim 1, wherein said glycerides are present in the form of an emulsion of the glyceride in aqueous phase.

14. Preparation according to claim 13, wherein said emulsion contains 2–30% fractionated soy oil, safflower oil, olive oil, fish oil, ruminant fat, cottonseed oil, sunflower oil, triglyceride with an unbranched carbon chain of medium length (MCT) and/or other physiologically acceptable triglycerides of vegetable, animal or synthetic origin.

15. Preparation according to claim 13, wherein said emulsion contains 0.5–10% acetylized mono- or diglycerides of saturated or unsaturated fatty acids with 6 to 24 carbon atoms.

16. Preparation according to claim 14, wherein said emulsion contains 0.5–10% acetylized mono- or diglycerides of saturated or unsaturated fatty acids with 6 to 24 carbon atoms.

* * * * *